(12) United States Patent
Sorensen (10) Patent No.: US 7,956,612 B2
(45) Date of Patent: Jun. 7, 2011

(54) SYSTEM AND METHOD FOR DISPLAYING MEDICAL IMAGING SPECTRAL DATA AS HYPSOMETRIC MAPS

(75) Inventor: Alma Gregory Sorensen, Lexington, MA (US)

(73) Assignee: The General Hospital Corporation, Boston, MA (US)

( * ) Notice: Subject to any disclaimer, the term of this patent is extended or adjusted under 35 U.S.C. 154(b) by 349 days.

(21) Appl. No.: 12/077,100

(22) Filed: Mar. 17, 2008

(65) Prior Publication Data

US 2008/0224700 A1 Sep. 18, 2008

Related U.S. Application Data

(60) Provisional application No. 60/918,590, filed on Mar. 16, 2007.

(51) Int. Cl.
*G01V 3/00* (2006.01)
(52) U.S. Cl. .......................... 324/307; 324/309; 324/318
(58) Field of Classification Search .......... 324/300–322; 600/407–435, 478; 342/195; 382/128–131
See application file for complete search history.

(56) References Cited

U.S. PATENT DOCUMENTS

| | | | |
|---|---|---|---|
| 3,376,499 A * | 4/1968 | Freeman | 324/312 |
| 4,081,742 A * | 3/1978 | Hofer et al. | 324/307 |
| 4,354,499 A * | 10/1982 | Damadian | 600/410 |
| 4,411,270 A * | 10/1983 | Damadian | 600/410 |
| RE32,619 E * | 3/1988 | Damadian | 600/410 |
| RE32,689 E * | 6/1988 | Damadian | 600/410 |
| 4,983,920 A | 1/1991 | Lampman et al. | |
| 5,739,807 A | 4/1998 | Thong | |
| 6,937,014 B2 * | 8/2005 | Sun et al. | 324/303 |
| 6,958,609 B2 * | 10/2005 | Raftery et al. | 324/321 |
| 7,102,354 B2 * | 9/2006 | Ardenkjaer-Larsen et al. | 324/321 |
| 7,265,712 B2 * | 9/2007 | Merkel et al. | 342/195 |
| 7,298,142 B2 * | 11/2007 | Hursan et al. | 324/303 |

(Continued)

FOREIGN PATENT DOCUMENTS

WO 2006/110768 10/2006

OTHER PUBLICATIONS

Leo L. Cheng et al, Metabolic Characterization of Human Prostate Cancer with Tissue Magnetic Resonance Spectroscopy, Cancer Res 2005; 65:(8), Apr. 15, 2005, pp. 3030-3034; www.aacrjournals.org.

(Continued)

*Primary Examiner* — Melissa J Koval
*Assistant Examiner* — Tiffany A Fetzner
(74) *Attorney, Agent, or Firm* — Quarles & Brady LLP (57) ABSTRACT

A system and method for displaying MR spectroscopy data acquired using a magnetic resonance imaging (MRI) system includes acquiring MR spectroscopy data from a region of interest using the MRI system. The MR spectroscopy data is processed to determine relative spectral amplitudes of each of a plurality of points in the MR spectroscopy data resulting from frequency components of molecules in the region of interest. Each of the plurality of points is mapped to a particular optical parameter based at least upon on the relative spectral amplitude associated with each point and a point is generated for each of the plurality of points having the optical parameter mapped thereto. The points for each of the plurality of points are arranged to form a hypsometric map.

42 Claims, 8 Drawing Sheets
(4 of 8 Drawing Sheet(s) Filed in Color)

U.S. PATENT DOCUMENTS

| | | | |
|---|---|---|---|
| 7,397,241 B2* | 7/2008 | Gauthausen et al. | 324/307 |
| 7,479,782 B2* | 1/2009 | Van Den Brink | 324/307 |
| 2004/0073120 A1* | 4/2004 | Motz et al. | 600/478 |
| 2004/0164738 A1* | 8/2004 | Raftery et al. | 324/321 |
| 2004/0189296 A1* | 9/2004 | Sun et al. | 324/306 |
| 2007/0043518 A1 | 2/2007 | Nicholson et al. | |
| 2008/0224700 A1* | 9/2008 | Sorensen | 324/309 |

OTHER PUBLICATIONS

K.W. Jordan et al; Metabolomic Imaging; 1 page, not dated.

PCT/US2008/057214 International Search Report dated Dec. 10, 2008.

K.W. Jordan et al; Metabolomic imaging; 1 page; submitted to the 2007 ISMRM, Berlin, May 19-25, 2007. Poster / Abstract 1895.

* cited by examiner

SYSTEM AND METHOD FOR DISPLAYING MEDICAL IMAGING SPECTRAL DATA AS HYPSOMETRIC MAPS

REFERENCE TO RELATED APPLICATIONS

This application is based on, incorporates herein by reference, and claims the benefit of provisional application Ser. No. 60/918,590, filed Mar. 16, 2007, and entitled "SYSTEM AND METHOD FOR DISPLAYING MEDICAL IMAGING SPECTRAL DATA AS HYPSOMETRIC MAPS."

BACKGROUND OF THE INVENTION

The field of the invention is magnetic resonance spectroscopy. More particularly, the invention relates to a system and method for displaying magnetic resonance spectroscopy data that facilitates the review and analysis of the spectroscopy data.

Magnetic resonance spectroscopy (MRS) uses the nuclear magnetic resonance (NMR) phenomenon to produce spectra of tissue components. When a substance such as human tissue is subjected to a uniform magnetic field (polarizing field $B_0$), the individual magnetic moments of the spins in the tissue attempt to align with this polarizing field, but precess about it in random order at their characteristic Larmor frequency. If the substance, or tissue, is subjected to a magnetic field (excitation field $B_1$) that is in the x-y plane and that is near the Larmor frequency, the net aligned moment, $M_z$, may be rotated, or "tipped," into the x-y plane to produce a net transverse magnetic moment $M_t$. A signal is emitted by the excited spins, and after the excitation signal $B_1$ is terminated, this signal may be received and processed to form a spectrum of a particular substance.

Magnetic Resonance Spectroscopy (MRS) may be used in vivo for the determination of individual chemical compounds located within a volume of interest. The underlying principle of MRS is that atomic nuclei are surrounded by a cloud of electrons that slightly shield the nucleus from any external magnetic field. As the structure of the electron cloud is specific to an individual molecule or compound, the magnitude of this screening effect is then also a characteristic of the chemical environment of individual nuclei. Since the resonant frequency of the nuclei is proportional to the magnetic field it experiences, the resonant frequency can be determined not only by the external applied field, but also by the small field shift generated by the electron cloud. Detection of this chemical shift, which is usually expressed as "parts per million" (PPM) of the main frequency, requires high levels of homogeneity of the main magnetic field $B_0$.

Typically, MR proton spectroscopy is used to generate a one-dimensional (1D) frequency spectrum representing the presence of certain chemical bonds in the region of interest. In medical diagnosis and treatment, MRS provides a non-invasive means of identifying and quantifying metabolites from a region of interest, often the human brain. For example, some metabolites of particular interest in proton MRS studies include glutamate/glutainine (Glx), choline (Cho), phosphocreatine ((P)Cr), N-acetylaspartate (NAA), and the inositols (mI and sI). By finding the relative spectral amplitudes resulting from frequency components of different molecules, medical professionals can identify chemical species and metabolites indicative of diseases, disorders, and other pathologies such as Alzheimer's disease, cancer, stroke, and the like.

Figure 1:
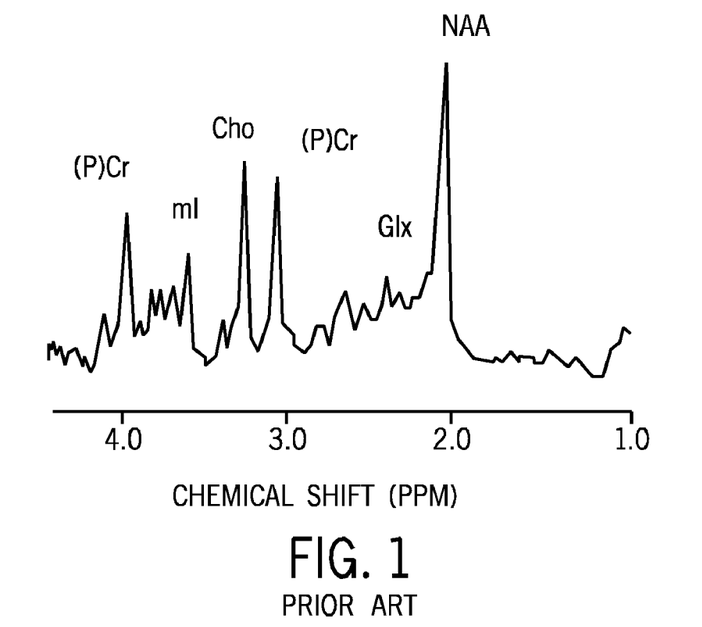
FIG. 1 is a traditional line graph of an MR spectrum generated using 1D MR spectroscopy.

For example, FIG. 1 shows a traditional 1D frequency spectrum line graph generated using MR spectroscopy. The data acquired using MRS spectroscopy is typically represented as a continuous spectrum that shows the relative spectral amplitudes of each chemical species and metabolite.

Figure 2:
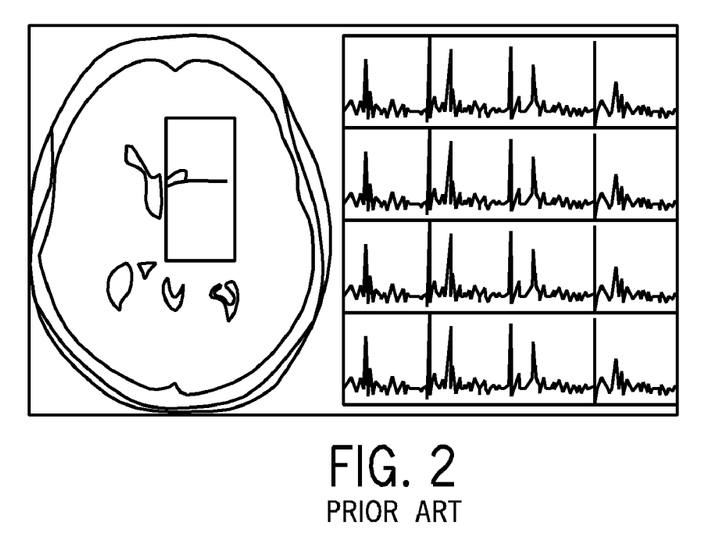
FIG. 2 is a traditional array of line graphs of traditional MR spectra generated using 2D MR spectroscopy.

While traditional spectral graphs generally allow a radiologist or physician to compare relative spectral amplitudes in a 1D-frequency spectrum, the task of comparing the relative amplitudes becomes more difficult when performing two-dimensional (2D) spectroscopy. In this case, the radiologist or physician must analyze multiple spectra, such as illustrated in FIG. 2, to discern subtle variations in the relative amplitude within each spectrum and between adjacent and non-adjacent spectra.

Therefore, it would be desirable to have a system and method for facilitating the review and analysis of data acquired with MR spectroscopy.

SUMMARY OF THE INVENTION

The present invention overcomes the aforementioned drawbacks by providing a system and method for displaying MR spectra that facilitates the comparison of relative spectral amplitudes within a single spectrum using 1D spectroscopy and between multiple spectra using 2D spectroscopy.

The present invention provides a system and method for displaying spectroscopy data as a hypsometric map indicating the relative spectral amplitudes as color variations through a given color gamut. More specifically, the amplitude at each chemical sift frequency is indicated by a line, or bar, of a particular color corresponding to the amplitude. Furthermore, the area under a particular portion of the curve may be reflected in a particular color coding or weighting. Accordingly, spectroscopy data is displayed in a manner that is more like the display of radiological imaging data and facilitates the comparison of relative spectral amplitudes within a single spectrum or across multiple spectra.

Various other features of the present invention will be made apparent from the following detailed description and the drawings.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

DESCRIPTION OF THE PREFERRED EMBODIMENT

Figure 3:
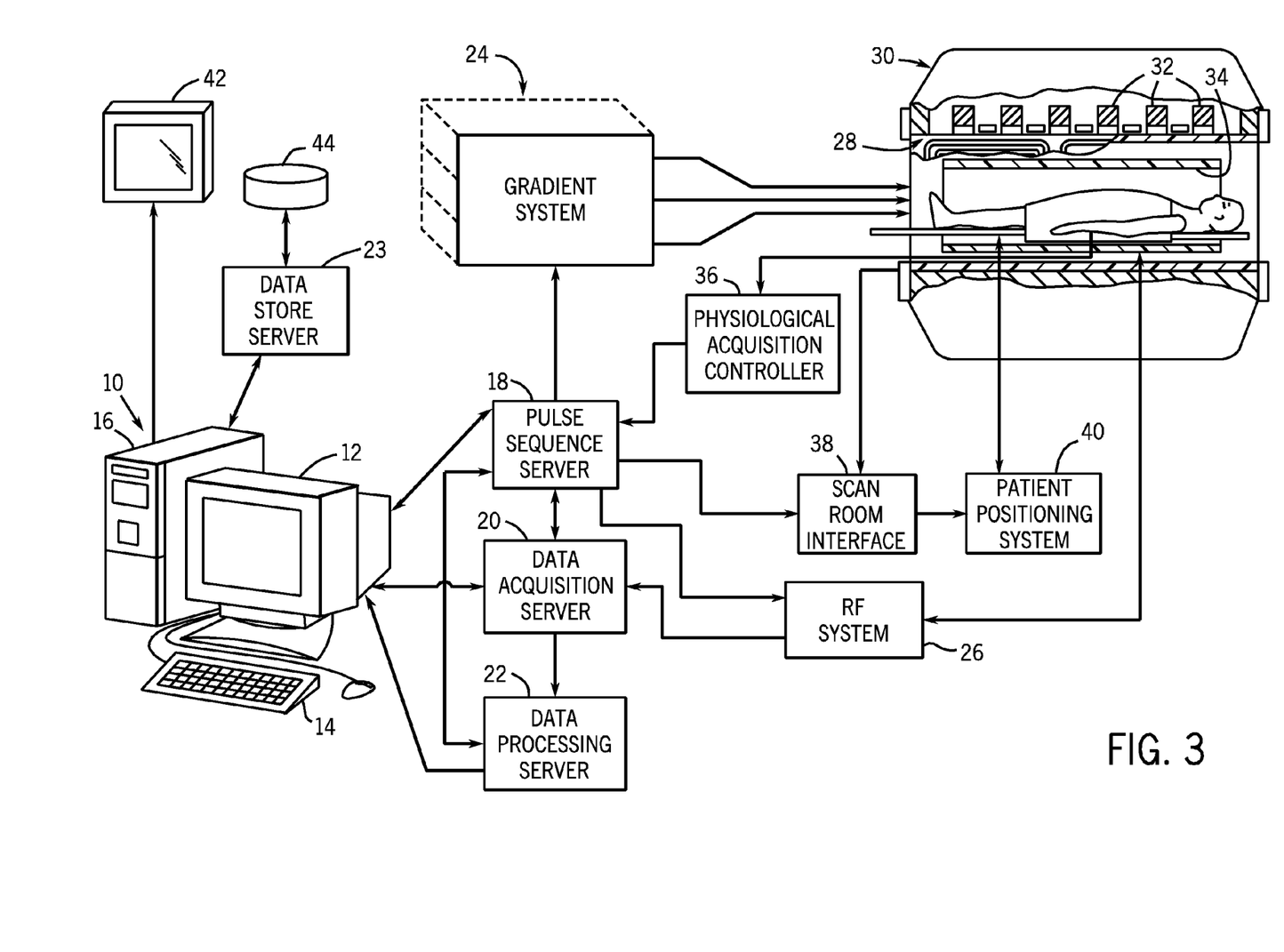
FIG. 3 is a block diagram of an MRI system that employs the present invention.

Referring particularly to FIG. 3, the present invention is employed using an MRI system. The MRI system includes a workstation 10 having a display 12 and a keyboard 14. The workstation 10 includes a processor 16 that is a commercially available programmable machine running a commercially available operating system. The workstation 10 provides the operator interface that enables scan prescriptions to be entered into the MRI system.

The workstation 10 is coupled to four servers: a pulse sequence server 18; a data acquisition server 20; a data processing server 22, and a data store server 23. In one embodiment, the workstation processor 16 and associated disc drive interface circuitry control the data store server 23. A separate processor controls the pulse sequence server 18, whereas the data acquisition server 20 and data processing server 22 may share a single processor. The workstation 10 and each of the servers 18, 20 and 22 are connected to a communications network. This network conveys data that is downloaded to the servers 18, 20 and 22 from the workstation 10, and it conveys data that is communicated between the servers.

The pulse sequence server 18 functions in response to instructions downloaded from the workstation 10 to operate a gradient system 24 and an RF system 26. Gradient waveforms necessary to perform the prescribed scan are produced and applied to the gradient system 24 that excites gradient coils in an assembly 28 to produce the magnetic field gradients $G_x$, $G_y$ and $G_z$ used for position encoding NMR signals. The gradient coil assembly 28 forms part of a magnet assembly 30 that includes a polarizing magnet 32 and a whole-body RF coil 34.

RF excitation waveforms are applied to the RF coil 34 by the RF system 26 to perform the prescribed magnetic resonance pulse sequence. Responsive NMR signals detected by the RF coil 34 are received by the RF system 26, amplified, demodulated, filtered, and digitized under direction of commands produced by the pulse sequence server 18. The RF system 26 includes an RF transmitter for producing a wide variety of RF pulses used in MR pulse sequences. The RF transmitter is responsive to the scan prescription and direction from the pulse sequence server 18 to produce RF pulses of the desired frequency, phase, and pulse amplitude waveform. The generated RF pulses may be applied to the whole body RF coil 34 or to one or more local coils or coil arrays.

The RF system 26 also includes one or more RF receiver channels. Each RF receiver channel includes an RF amplifier that amplifies the NMR signal received by the coil to which it is connected and a quadrature detector which detects and digitizes the I and Q quadrature components of the received NMR signal. The magnitude of the received NMR signal may thus be determined at any sampled point by the square root of the sum of the squares of the I and Q components:

$$M = \sqrt{I^2 + Q^2} \quad (1),$$

and the phase of the received NMR signal may also be determined:

$$\Phi = \tan^{-1} Q/I \quad (2).$$

The pulse sequence server 18 also optionally receives patient data from a physiological acquisition controller 36. The controller 36 receives signals from a number of different sensors connected to the patient, such as ECG signals from electrodes or respiratory signals from a bellows. Such signals are typically used by the pulse sequence server 18 to synchronize, or "gate" the performance of the scan with the subject's respiration or heart beat.

The pulse sequence server 18 is also connected to a scan-room interface circuit 38 that receives signals from various sensors associated with the condition of the patient and the magnet system. It is also through the scan room interface circuit 38 that a patient positioning system 40 receives commands to move the patient to desired positions during the scan.

The digitized NMR signal samples produced by the RF system 26 are received by the data acquisition server 20. The data acquisition server 20 operates in response to instructions downloaded from the workstation 10 to receive the real-time NMR data and provide buffer storage such that no data is lost by data overrun. In some scans, the data acquisition server 20 does little more than pass the acquired NMR data to the data processor server 22. However, in scans that require information derived from acquired NMR data to control the further performance of the scan, the data acquisition server 20 is programmed to produce such information and convey it to the pulse sequence server 18. For example, during prescans NMR data is acquired and used to calibrate the pulse sequence performed by the pulse sequence server 18. Also, navigator signals may be acquired during a scan and used to adjust RF or gradient system operating parameters or to control the view order in which the k-space is sampled. And, the data acquisition server 20 may be employed to process NMR signals used to detect the arrival of a contrast agent in an MRA scan. In all these examples, the data acquisition server 20 acquires NMR data and processes it in real-time to produce information which is used to control the scan.

The data processing server 22 receives NMR data from the data acquisition server 20 and processes it in accordance with instructions downloaded from the workstation 10. Such processing may include, for example: Fourier transformation of raw k-space NMR data to produce two or three-dimensional images; the application of filters to a reconstructed image; the performance of a backprojection image reconstruction of acquired NMR data; the calculation of functional MR images; the calculation of motion or flow images, and the calculation of spectroscopy images according to the present invention.

Images and/or spectroscopy processed by the data processing server 22 are conveyed back to the workstation 10 where they are stored. Real-time images are stored in a data base memory cache (not shown) from which they may be output to operator display 12 or a display 42 that is located near the magnet assembly 30 for use by attending physicians. Batch mode images, selected real-time images, and/or spectroscopy data are stored in a host database on disc storage 44. When such images have been reconstructed and transferred to storage, the data processing server 22 notifies the data store server 23 on the workstation 10. The workstation 10 may be used by an operator to archive the images or spectroscopy data, produce films, or send the images via a network to other facilities.

As described above with respect to FIGS. 1 and 2, data acquired when performing an MR spectroscopy procedure on a region of interest using the above-described MRI system is typically displayed as a graph of a frequency spectrum (or spectra) indicating the presence of specific chemical compound in the region of interest. A radiologist or physician then reviews the relative spectral amplitudes present in the graph to identify indicators of different compounds.

The traditional line-graph presentation of each frequency spectrum has a number of drawbacks. First, the display of information in a line-graph format is very different from the display formats used for the majority of information associated with radiological procedures. That is, radiologists and physicians are trained to analyze and accustomed to reviewing medical images that illustrate information by way of color variations or "contrast". On the other hand, when reviewing traditional line-graph presentations of MR spectroscopy data, the radiologist or physician must compare portions of the line graph to determine the relative height of each portion and the significance indicated by subtle difference in height. Furthermore, they must make subtle determinations about the specific alignment of a particular point in the line graph along a segmented axis indicating the exact chemical shift indicated by the particular point in the line graph.

Second, when analyzing and comparing multiple spectra, such as generated when performing a 2D MR spectroscopy procedure, these counterintuitive analysis techniques become extremely difficult. For example, referring to FIG. 2, a physician or radiologist must not only compare portions of a single line graph to determine the relative height of each portion and make subtle determinations about the exact chemical shift indicated by a particular point in the single line graph, but must extend this procedure to multiple, individual line graphs. Thus, the physician or radiologist must perform these same comparisons and analysis across and between the multiple, individual line graphs.

Figure 4:
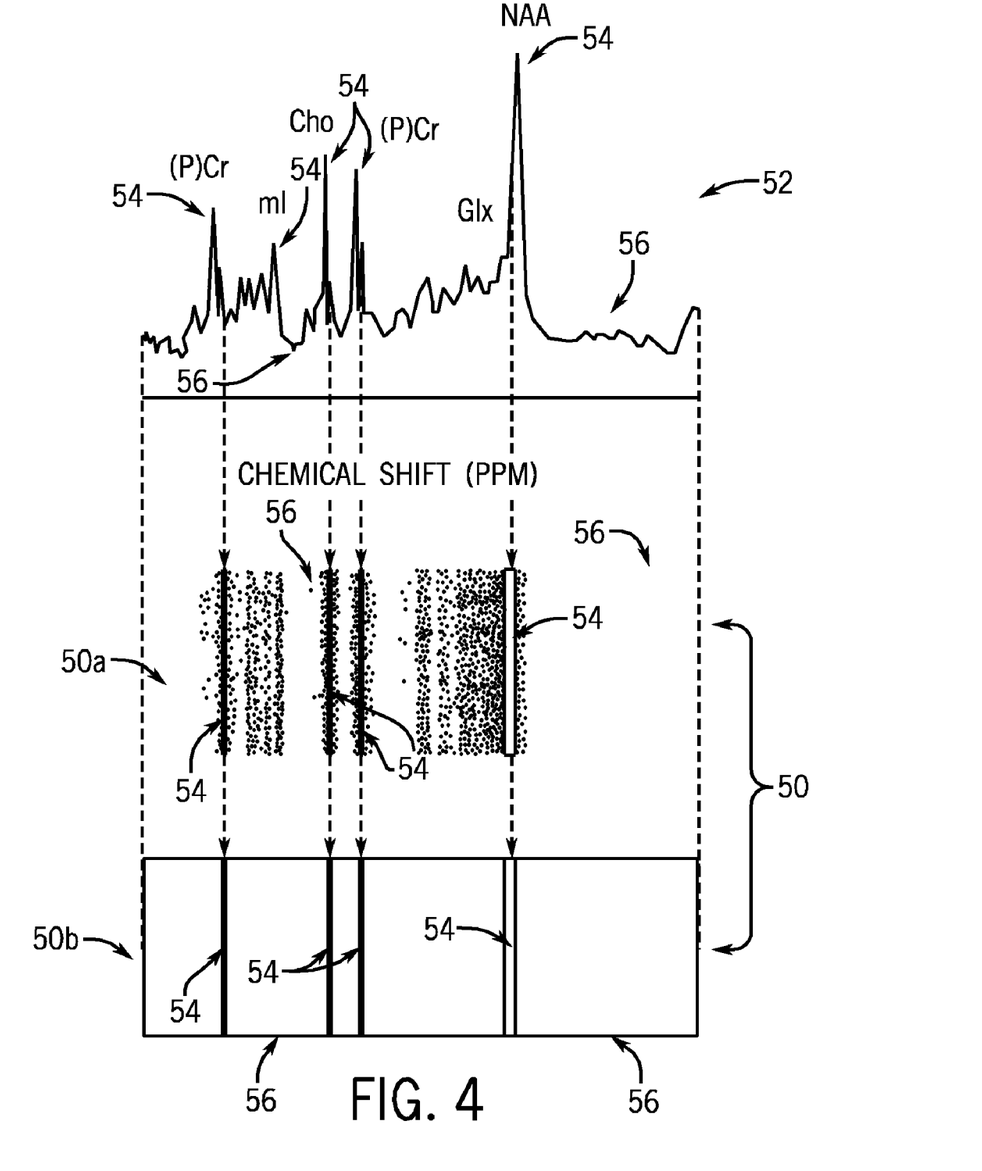
FIG. 4 is an illustration of two hypsometric maps of a common MR spectrum generated using 1D spectroscopy, in accordance with the present invention, and correlated with a traditional graph of the common MR spectrum.

The present invention provides a system and method for displaying MR spectroscopy data in a manner that is intuitive to radiologists and physicians trained to analyze medical images. Referring to FIG. 4, the present invention provides a new system and method for displaying MR spectroscopy data referred to hereafter as a hypsometric map 50. The hypsometric map 50 is produced by mapping the amplitude and/or a chemical shift of the spectroscopic signal at each frequency in the spectrum to a parameter that corresponds to the signal amplitude/chemical shift. A line or bar having a particular optical parameter is produced on the display and the process is repeated for each frequency to produce a series of contiguous lines or bars. As shown in FIG. 4, the optical parameter can be embodied as specific color and/or an intensity, a modulation, a saturation, or a hue of a given color.

Through one or a combination of these optical parameters, variations in spectral values in the MR spectroscopy data which were traditionally displayed as peaks 54 and valleys 56 in a line graph 52, can be illustrated in a hypsometric map 50 to convey a wide variety of information in a format that is more like the display of radiological imaging data. Accordingly, the hypsometric map 50 displays the MR spectroscopy data in a manner that allows radiologists and physicians to employ analysis techniques useful when reviewing medical images.

For example, a color gamut for use in creating the hypsometric map 50 may be selected to resemble a grey-scale medical image. In this case, the relative spectral amplitudes may be shown as color variations in a hypsometric map 50a created using a "negative" (black-on-white) color gamut or a hypsometric map 50b created using a "positive" (black-on-white) color gamut. However, it is contemplated that the hypsometric map 50 may employ any color gamut. For example, a hypsometric map 50 may be created using a color gamut including all of the primary colors or any other set of colors. In this case, relative amplitude may not only be indicated by variations in contrast created by color variations, but also optical parameters such as intensity, modulation, saturation, hue and/or tone.

Figure 6:
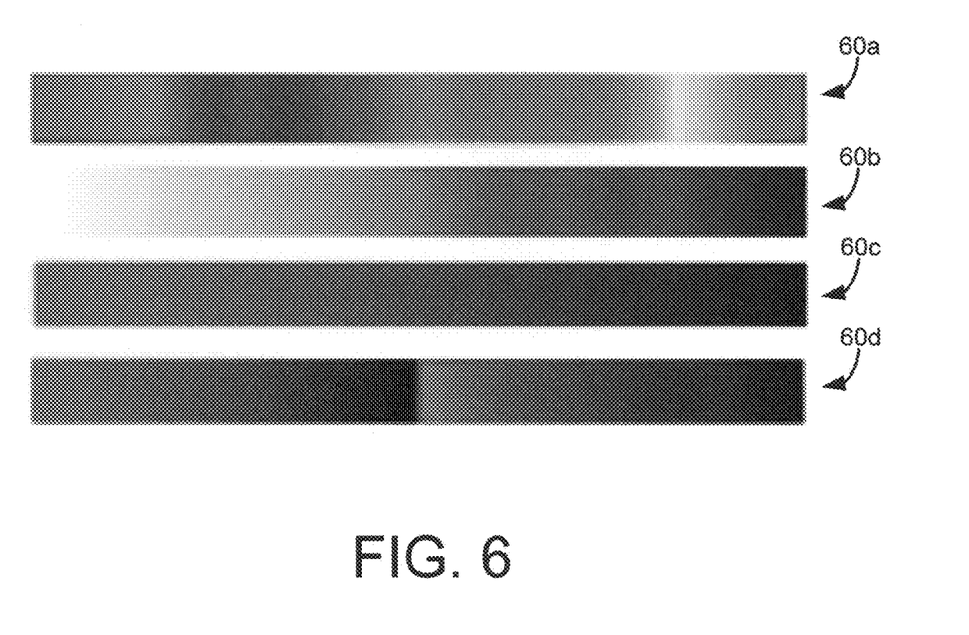
FIG. 6 is an illustration of a plurality of hypsometric maps having various configurations in accordance with the present invention.
Figure 7A:
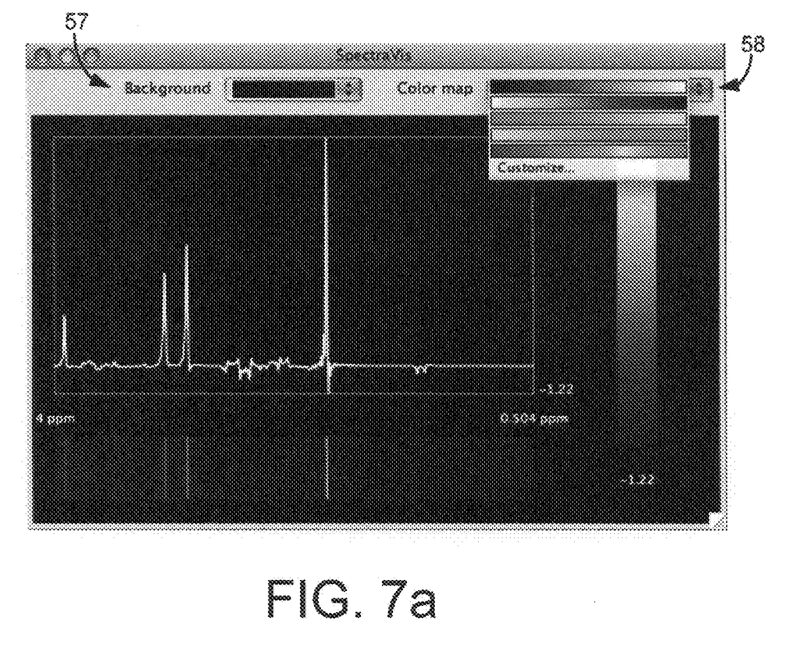
FIGS. 7a and 7b are further screen shots of the application and user interface of FIGS. 5a and 5b and illustrating a user interface for selecting varied color parameters in accordance with the present invention.
Figure 7B:
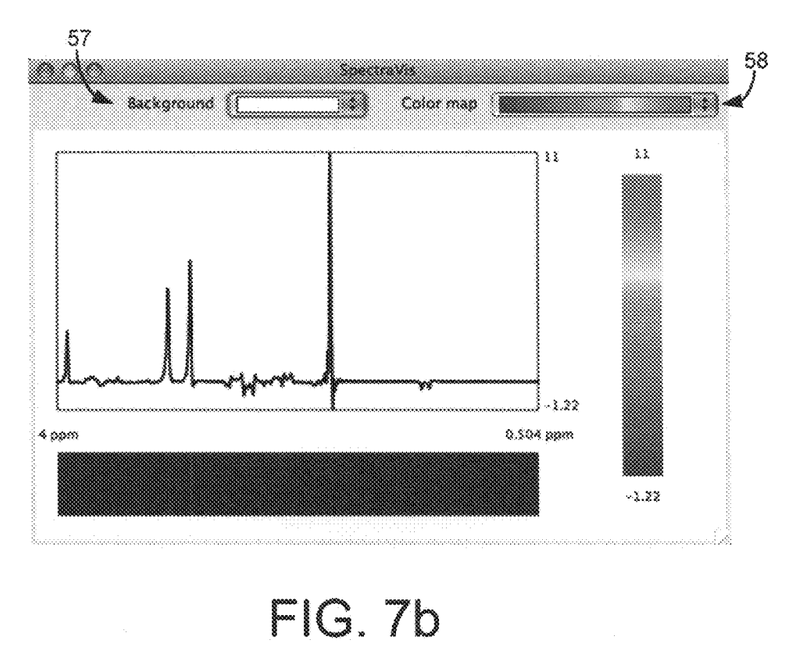

These optical parameters can be selected or mapped to display a wide variety of information. For example, referring to FIGS. 4 and 7, a plurality of look up tables or maps can be stored and selected to display data in a desired hypsometric map format. As will be described below with respect to FIG. 6, when processing the acquired MR spectroscopy data, the relative spectral amplitude and chemical shift associated with a point in the MR spectroscopy data is determined. Based on one or both of these characteristics, each point in the MR spectroscopy data can be mapped to a particular optical parameters. As described above, FIG. 4 shows a pair of hypsometric maps 50a, 50b created by mapping each point of data to color displayed as line. The lines are then arranged to make a contiguous spectrum showing the relative amplitude of each point through a color and/or intensity variation.

Figure 5A:
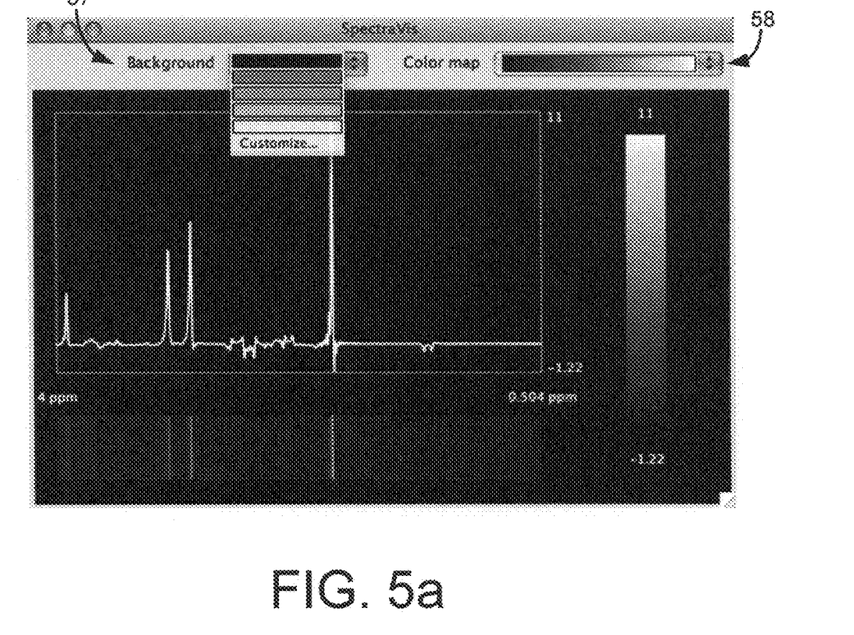
FIGS. 5a and 5b are screen shots of an application and user interface for creating and manipulating the display particulars of the hypsometric maps in accordance with the present invention.
Figure 5B:
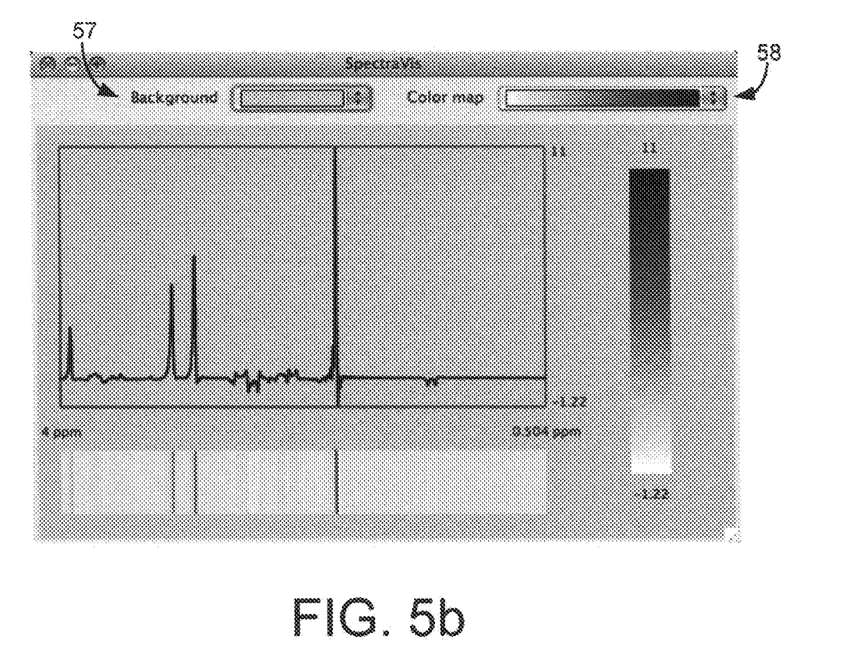

As illustrated in FIGS. 5a and 5b, it is contemplated that the specific contrast elements may be user-selected. For example, it is contemplated, as illustrated in FIG. 5a, that a user interface may be provided that allows a user to select a desired background color. Specifically, as illustrated, a default background may be black and, thus, contrast is illustrated with grayscale variations, with white representing the highest contrast element. However, a user may use a selection interface 57 to change the background color. Accordingly, as illustrated in FIG. 5b, the system automatically changes the contrast elements as needed.

Similarly, it is contemplated that the color map parameters may be user selected using a color map selection interface 58. Beyond grayscale, in a variety of application, color gamuts may be desirable. For example, referring to FIG. 6, a variety of color gamuts 60a, 60b, 60c, 60d may be utilized to further highlight and illustrate information. For example, referring to FIGS. 7a and 7b, beyond the hypsometric maps 50a, 50b illustrated in FIG. 4 and created using a grey-scale color gamut, a color map menu 58 is provided that allows the selection of colors other than black, white, and grey. It is contemplated that specific colors can be mapped to a particular chemical shift. In this case, other optical parameters, such as color intensity, a color modulation, a color saturation, color tone, and a color hue may be used to indicate spectral amplitude variations.

For example, a chemical shift corresponding to a particular molecule of interest, such as NAA or Cho, may be illustrated by the color blue and red, respectively. To illustrate an amplitude variation within the area of chemical shift corresponding to NAA or Cho, other optical properties, such as the intensity, hue, or tone, may be varied. Within the present example, increased spectral amplitude within the NAA chemical shift region may be illustrated by intensifying the blue color or lightening the hue or tone of the blue color. On the other hand, decreased spectral amplitude within the NAA chemical shift region may be illustrated by decreasing the intensity or darkening the hue or tone of the blue color.

Furthermore, it is contemplated that certain colors may be used to show the amount of area under a particular curve. That is, whereas brightness or thickness of a line in the hypsometric map may correspond to the amplitude or magnitude of a particular peak in the chemical shift line graph, the color used may represent the size of the area under the curve corresponding to that particular peak. For example, green might be used to illustrate a relatively small area under the curve, whereas red is used to illustrate a large area under the curve.

Figure 8:
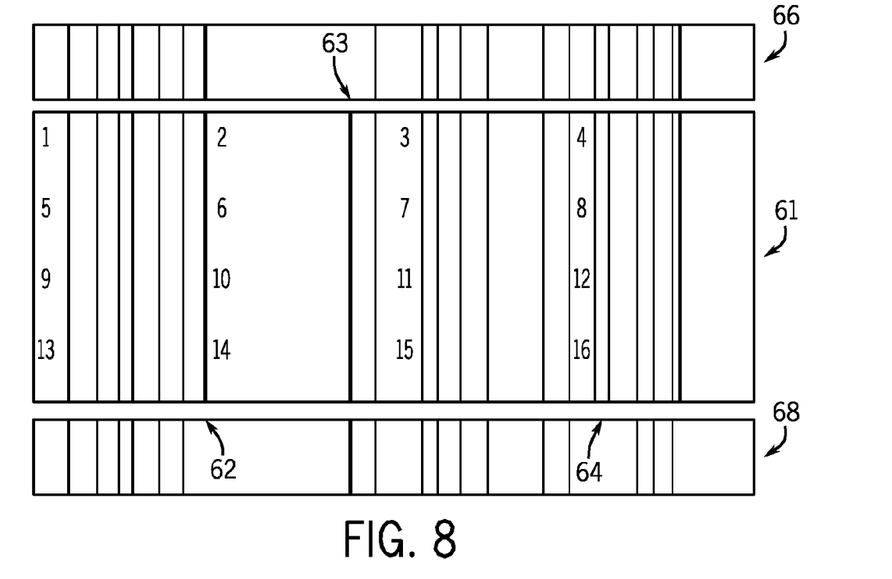
FIG. 8 is an array of hypsometric maps of MR spectra generated using 2D spectroscopy, in accordance with the present invention.

The present invention not only facilitates the analysis of individual spectrum generated using 1D MR spectroscopy, but also the analysis and comparison of multiple spectra, such as generated using 2D MR spectroscopy. Referring now to FIG. 8, a plurality of hypsometric maps may be arranged in an array 61. By arraigning the plurality of hypsometric maps in the array 61 in a horizontal alignment or, as shown in FIG. 8, a vertical alignment, contrast areas corresponding to peaks or valleys in a traditional line-graph representation of the MR spectroscopy data are aligned. That is, areas of contrast 62, 63, 64 are aligned and registered by arranging the plurality of hypsometric maps in the array 61, thereby allowing ready comparison of relative spectral variations between each hypsometric map in a given row, when horizontally aligned, or in a given column, when vertically aligned.

Additionally, reference hypsometric maps 66, 68 may be provided to further aid analysis and diagnosis. For example, a "normal" hypsometric map 66 may be aligned along one side of the array 61 and a "diagnosis" hypsometric map 68 may be aligned along another side of the array 61. When performing an analysis of the array 61, a ready comparison can be made between each column (or row) of the array 61 and a corresponding portion of the set of normal or diagnosis hypsometric maps 66, 68. In the example illustrated in FIG. 8, the set of normal hypsometric maps 66 indicates that two of the areas of contrast 62, 64 are within the "normal" range. On the other hand, one area of contrast 63 in the array 61 indicates the pathology reflected in the diagnostic hypsometric map 68. Additional reference information, such as chemical markers, or even a traditional reference line graph, may also arranged about the periphery of the array 61 or overlaid on the array 61. Accordingly, radiologists and physicians can quickly and easily compare multiple hypsometric maps and determine whether a particular area of contrast within a particular hypsometric map or spanning multiple hypsometric maps corresponds is in a normal range or indicative of a particular pathology.

Figure 9:
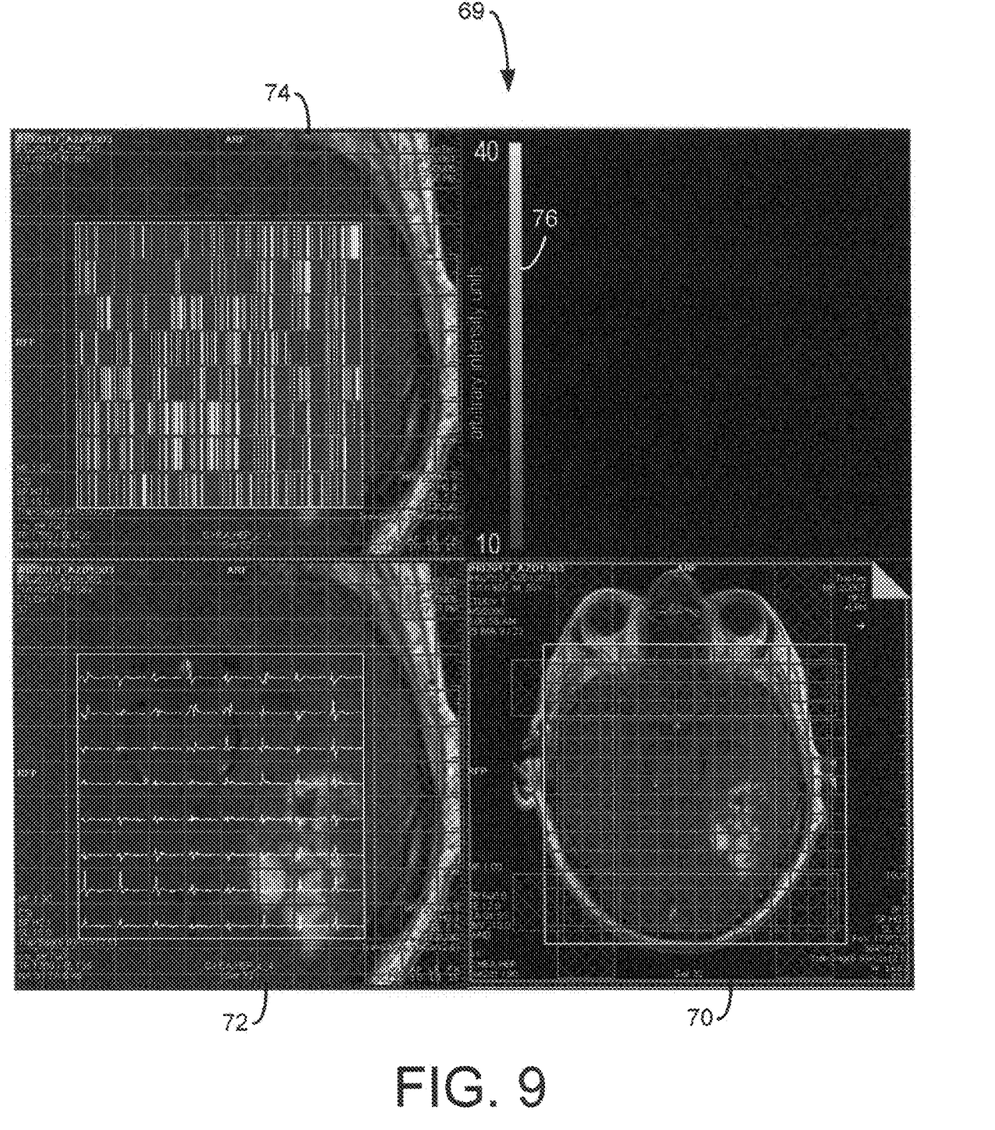
FIG. 9 are screen shots of an integrated spectroscopy data viewing system.

Referring now to FIG. 9, again, it is contemplated that a review system 69 may include a variety of correlated informational data. Furthermore, within this set of correlated data, color may be used to more clearly convey information or to provide additional information. For example, it is contemplated that the review system may include images 70 acquired during an MRI scout scan. In the illustrated image 70, a tumor can be seen. This view may be coupled with corresponding spectroscopy data. For example, a traditional spectroscopy display 72 may be provided. In addition, an array of color hypsometric maps 74 displaying the spectroscopy data associated with the image 70 may also be included along with a color key 76.

It is contemplated, that the color may be used to display a variety of information. For example, the color may include information related a chemical shift corresponding to a particular molecule of interest, such as NAA or Cho. Additionally or alternatively, an amplitude variation within the area of chemical shift corresponding to NAA or Cho may be illustrated in the intensity of the color. In addition, the "size" or width of the colors may be used to show the amount of area under a particular curve. It is contemplated that the particular features (for example, color, hue, intensity, width, and the like) may be used to convey different information in different viewing applications and/or may be user selectable. For example, when reviewing an array of relatively small hypsometric maps, such as in a view similar to that illustrated in FIG. 9, it may be advantageous to use colors and weightings (using intensity, hue, size, and the like) to convey the most relevant or desired information clearly, despite the relatively small size of the individual hypsometric maps in the array.

Figure 10:
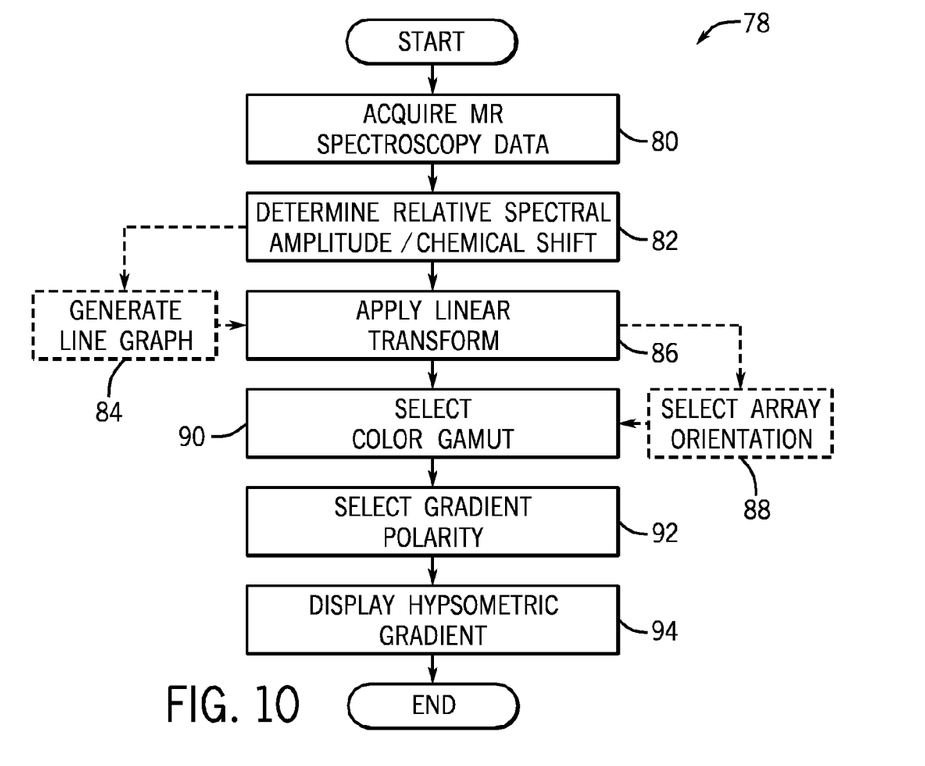
FIG. 10 is a flow chart setting forth the steps for generating one or more hypsometric maps from data acquired using MR spectroscopy or converting traditional graphed MR spectra into hypsometric maps.

Referring to now FIG. 10, a process 78 performed by the above-described data processing server 22 for generating one or more of the above-described hypsometric maps from MR spectroscopy data begins at process block 80 with the prescription and acquisition of MR spectroscopy data. The MR spectroscopy data is acquired using an MR system, as described above, and once the data is acquired, data processing is performed at process bock 82 to determine the relative spectral amplitudes and chemical shift associated with each point of data acquired.

Thereafter, a traditional line graph may be generated from the acquired spectroscopy data at process block 84. In this case, the traditional line graph may be used to analyze the area under the curve portion associated with a particular area of interest. However, a traditional line graph need not be generated in all embodiments. Rather, the generation of a traditional line graph at process block 84 may be optionally selected during the process 78 or may be performed when the present invention is used to retrofit a traditional system configured to generate line graphs from the MR spectroscopy data. Furthermore, a traditional line graph may be employed when converting archived spectroscopy data that has been saved as a traditional line graph to one or more hypsometric maps.

In any case, a linear transform is applied to the data at process block 86 to convert the data to a hypsometric map in which successive points on the line graph (i.e., signal amplitudes at successive frequencies) are mapped to a color or grey-scale value corresponding to the signal amplitude. These produce successive lines, or bars, in the hypsometric map. Additionally, it may be necessary to normalize the data based on a mean or peak amplitude value included in the data in order to provide a desired amount of contrast within the hypsometric map or to weight particular areas of contrast to emphasize a particular portion of data.

As described above with respect to FIGS. 8 and 9, the hypsometric maps may be output to a display and arranged in a vertical or horizontal orientation with the array 58. If the spectroscopy data was acquired using a 2D spectroscopy process, the user may select an orientation for the hypsometric maps in the array at process block 88.

Before displaying an image of the hypsometric map, a user may select the desired optical parameters that are to be mapped to each point of the MR spectroscopy data. For example, a user may select a desired color gamut at process block 90. A plurality of look up tables may be provided that are used to select and map each point to a specific color or grey-scale value based on the amplitude values and/or chemical shift associated with each point. For example, as described above, a user may select a desired background and may select between a grey-scale based gamut and a gamut including a variety of colors. Furthermore, if a gamut including a variety of colors is selected, a user may select the particular set of colors included in the color gamut and/or the specific mapping of particular colors to chemical shifts associated with metabolites of interest. It is contemplated that a variety of preset color gamut profiles may be provided that are designed to highlight different sets of data. Alternatively, it is contemplated that a user may select each of the colors to be utilized.

Additionally, a user may select a polarity of the map at process block 92. For example, a user may select a negative polarity image having a light background with contrast areas indicated in dark colors or a positive polarity image having a dark background with contrast areas indicated in light colors.

Once the use-selected display parameters are selected, the hypsometric map(s) is displayed at process block 94 and the process 78 is complete.

Therefore, a system and method for displaying data acquired during an MR spectroscopy process is provided that facilitates analysis and comparison with multiple data sets. In particular, the present invention provides one or more hypsometric maps generated from acquired data or traditional line graphs created from MR spectroscopy data. The hypsometric maps indicate the relative spectral amplitudes of molecule or compound within an area of interest as color variations through a given color gamut.

The present invention has been described in terms of the preferred embodiment, and it should be appreciated that many equivalents, alternatives, variations, and modifications, aside from those expressly stated, are possible and within the scope of the invention. Therefore, the invention should not be limited to a particular described embodiment.

What is claimed is:

1. A method for displaying MR spectroscopy data acquired using a magnetic resonance imaging (MRI) system, the method comprising the steps of:
    a) acquiring MR spectroscopy data from a region of interest using the MRI system;
    b) determining a signal spectral amplitude associated with each of a plurality of points in the MR spectroscopy data resulting from frequency components of molecules in the region of interest;
    c) mapping each of the plurality of points to a particular optical parameter based at least on at least one of the signal spectral amplitude associated with each point and an area under a series of adjacent points in the plurality of points, the particular optical parameter including at least one of color, color intensity, color modulation, color saturation, color tone, and color hue;
    d) generating a parameter point for each of the plurality of points having the optical parameter mapped in step c); and
    e) arranging the parameter points to display a hypsometric map, wherein the hypsometric map facilitates the analysis and comparison of MR characteristics within the region of interest.

2. The method of claim 1 wherein step d) further includes generating a plurality of parameter points arranged to form a line for each of the plurality of points in the MR spectroscopy data, wherein the plurality of parameter points arranged to form the line share the optical parameter mapped in step c).

3. The method of claim 2 wherein step e) further includes arranging the lines together to display the hypsometric map.

4. The method of claim 1 further comprising step f) selecting at least one of a vertical orientation and a horizontal orientation for display of the hypsometric map.

5. The method of claim 1 wherein step b) includes determining a chemical shift associated with each of the plurality of points in the MR spectroscopy data and wherein step c) further includes mapping each of the plurality of points to a particular optical parameter based on a combination of the signal spectral amplitude and the chemical shift associated with each of the plurality of points.

6. The method of claim 1 wherein the color includes at least one of black, white, grey, and primary colors.

7. The method of claim 1 wherein step b) further includes determining a chemical shift associated with each of the plurality of points in the MR spectroscopy data and wherein step c) includes mapping each of the plurality of points, having an associated chemical shift corresponding to a particular metabolite, to a predetermined color.

8. The method of claim 7 wherein step c) further includes mapping one of a color intensity, a color modulation, a color saturation, a color tone, and a color hue to each of the plurality of points based on the signal spectral amplitude, associated with each of a plurality of points determined in step b) and the predetermined color.

9. The method of claim 7 wherein the predetermined color is user selectable.

10. The method of claim 1 wherein step wherein step b) includes generating a line graph from the MR spectroscopy data.

11. The method of claim 1 including applying a linear transform to the MR spectroscopy data and normalizing the transformed MR spectroscopy data about one of a peak signal amplitude and a mean signal amplitude.

12. The method of claim 10 further comprising step f) displaying at least one reference hypsometric map proximate to the line graph.

13. The method of claim 12 wherein the at least one reference hypsometric map indicates one of a normal MR spectrum and an MR spectrum indicative of a given pathology.

14. A method for displaying MR spectroscopy data acquired using a magnetic resonance imaging (MRI) system, the method comprising the steps of:
    a) acquiring MR spectroscopy data from a region of interest using the MRI system;
    b) processing the MR spectroscopy data to determine portions of the MR spectroscopy data corresponding to frequency components of molecules in the region of interest; and
    c) displaying a hypsometric map of an MR spectrum generated from at least a portion of the MR spectroscopy data corresponding to frequency components of molecules in the region of interest, the hypsometric map representing the MR spectrum as two-dimensional color variations through a given color gamut thereby aiding visual analysis and comparison of MR characteristics within the region of interest.

15. The method of claim 14 wherein step b) further includes generating a line graph of the MR spectrum and applying a linear transform to convert a position of each point on the line graph to a color in the given color gamut.

16. The method of claim 14 wherein step b) further includes mapping each point in the MR spectroscopy data to a particular color in the color gamut based on a chemical shift associated with each point.

17. The method of claim 16 wherein step b) further includes mapping at least one of color intensity, color modulation, color saturation, color tone, and color hue of the particular color to each point in the MR spectroscopy data.

18. The method of claim 14 wherein step b) further includes mapping points, in the MR spectroscopy data, that have a chemical shift associated with a particular metabolite to a predetermined color in the color gamut.

19. The method of claim 14 wherein step b) further includes determining relative spectral amplitudes resulting from frequency components of molecules in the region of interest and mapping at least one of color intensity, color modulation, color saturation, color tone, and color hue of the mapped color to each point in the MR spectroscopy data based on the determined relative spectral amplitudes.

20. The method of claim 14 wherein the color gamut is a grey-scale color gamut.

21. The method of claim 14 wherein increased relative spectral amplitudes are illustrated in light colors in the hypsometric map.

22. The method of claim 14 wherein increased relative spectral amplitudes are illustrated in dark colors in the hypsometric map.

23. The method of claim 14 further comprising step d) arranging at least one reference hypsometric map proximate to the hypsometric map generated from the spectroscopy data.

24. The method of claim 23 wherein the at least one reference hypsometric map indicates one of a normal MR spectrum and an MR spectrum indicative of a given pathology.

25. The method of claim 14 wherein step a) further includes acquiring one-dimensional (1D) spectroscopy data.

26. The method of claim 14 wherein step a) further includes acquiring two-dimensional (2D) spectroscopy data.

27. The method of claim 26 wherein step c) further includes displaying a plurality of MR spectra derived from 2D spectroscopy data in an array of hypsometric maps.

28. The method of claim 27 wherein step c) further includes arranging the hypsometric maps in a horizontally aligned array.

29. The method of claim 27 wherein step c) further includes arranging the hypsometric maps in a vertically aligned array.

30. The method of claim 14 wherein the color gamut includes black and white.

31. The method of claim 14 wherein in the color gamut includes primary colors.

32. The method of claim 14 wherein step b) further includes creating a line graph of the MR spectrum and determining at least one area under a portion of the line graph corresponding to frequency components of molecules in the region of interest and wherein step e) includes indicating the at least one area through one of color, hue, intensity, and tone variations.

33. The method of claim 32 wherein step c) further includes displaying at least one of the line graph of the MR spectrum and chemical marks along a periphery of the hypsometric map.

34. A method for displaying magnetic resonance (MR) spectroscopy data acquired using a magnetic resonance imaging (MRI) system, the method comprising steps of:
a) acquiring MR spectroscopy data from a region of interest using the MRI system;
b) determining a signal spectral amplitude associated with each of a first plurality of data points in the MR spectroscopy data;
c) assigning an optical parameter to each of adjacent data points of the first plurality based on at least one of the associated signal spectral amplitude and an area under a curve formed by a sequence of adjacent data points of the first plurality;
d) for each of the adjacent data points of the first plurality, generating a substantially straight geometric line having a corresponding assigned optical parameter; and
e) displaying a first hypsometric map of the first plurality of data points in the MR spectroscopy data, the first hypsometric map including the generated geometric lines arranged in a sequence corresponding to the sequence of adjacent data points of the first plurality, thereby permitting visual analysis and comparison of MR characteristics within the region of interest.

35. The method of claim 34 further comprising steps of:
f) repeating steps of assigning and generating for a second plurality of data points in the MR spectroscopy data; and
g) displaying a second hypsometric map of the second plurality of data points in the MR spectroscopy data, the second hypsometric map including geometric lines generated for the second plurality of data points and arranged in a sequence corresponding to the sequence of adjacent data points of the second plurality of data points,
wherein the first and second hypsometric maps are displayed in an array of maps that represents two-dimensional (2D) MR spectroscopy data.

36. The method of claim 34 further comprising step f) selecting at least one of a vertical orientation and a horizontal orientation for display of the first hypsometric map.

37. The method of claim 34, wherein step b) includes determining a chemical shift associated with each of the first plurality of data points and wherein step c) includes assigning an optical parameter to each of adjacent data points of the first plurality based on a combination of the corresponding associated signal spectral amplitude and chemical shift.

38. The method of claim 34, wherein the optical parameter includes at least one of color, color intensity, color modulation, color saturation, color tone, and color hue.

39. The method of claim 34, wherein step b) includes determining a chemical shift associated with each of the first plurality of data points in the MR spectroscopy data and wherein step c) includes assigning a predetermined color to each of the first plurality of data points that has an associated chemical shift corresponding to a particular metabolite.

40. The method of claim 34, wherein step c) includes assigning at least one of color intensity, color modulation, color saturation, color tone, and color hue to each of the first plurality of data points based on the corresponding associated signal spectral amplitude and predetermined color.

41. The method of claim 34 comprising applying a linear transform to the MR spectroscopy data and normalizing the transformed MR spectroscopy data about one of a peak signal amplitude and a mean signal amplitude.

42. The method of claim 34 further comprising step f) displaying at least one of a curve formed by a sequence of adjacent data points of the first plurality and at least one reference hypsometric map proximate the first hypsometric map, the at least one reference hypsometric map representing one of a normal MR spectrum and an MR spectrum indicative of a given pathology.

* * * * *